United States Patent [19]

Schumacher et al.

[11] 4,113,574
[45] Sep. 12, 1978

[54] ACRYLIC POLYMERIZATION INHIBITION

[75] Inventors: Ignatius Schumacher, Webster Groves, Mo.; James E. White, Coshocton, Ohio

[73] Assignee: Monsanto Company, St. Louis, Mo.

[21] Appl. No.: 734,893

[22] Filed: Oct. 22, 1976

[51] Int. Cl.$^2$ .................. B01D 3/34; C07C 57/04; C07C 69/54
[52] U.S. Cl. .................................. 203/8; 203/62; 203/DIG. 21; 562/598; 260/346.76; 560/4
[58] Field of Search ......... 260/526 N, 346.76, 346.75; 560/4; 203/8, 6, 7, 9, 38, 62, 54, DIG. 21

[56] References Cited

U.S. PATENT DOCUMENTS

| | | | |
|---|---|---|---|
| 2,386,365 | 10/1945 | Staudinger et al. | 260/526 N |
| 3,169,911 | 2/1965 | Vogt et al. | 203/8 |
| 3,227,628 | 1/1966 | Hess | 260/526 N |
| 3,261,847 | 7/1966 | Sullivan | 260/346.76 |
| 3,965,123 | 6/1976 | Franklin | 260/346.76 |
| 4,010,082 | 3/1977 | Nemec et al. | 260/526 N |
| 4,021,310 | 5/1977 | Schimizu et al. | 203/8 |

Primary Examiner—Wilbur L. Bascomb, Jr.
Attorney, Agent, or Firm—James C. Logoansini; Paul L. Passley; Stanley M. Tarter

[57] ABSTRACT

The prior art discloses a number of polymerization inhibitors for acrylic acid, acrylates and derivatives thereof, but such polymerization inhibitors have low vapor pressures. Consequently, when acrylic acid is vaporized, it tends to polymerize on cooling surfaces causing undesirable deposits on storage vessels and the like. However, when a polymerization inhibiting amount of 2,4-pentanedione is added to the monomer, the polymerization of acrylic acid on cooling surfaces is inhibited.

4 Claims, No Drawings

ACRYLIC POLYMERIZATION INHIBITION

BACKGROUND OF THE INVENTION

This invention relates to methods of preventing the polymerization of acrylic acid and acrylate derivatives, and to acrylic acid and acrylate derivatives comprising a small amount of a polymerization inhibitor.

The prior art discloses that any number of derivatives of 2,4-pentanedione can be used for the production of acrylic acid and its functional derivatives (see, for example, U.S. Pat. Nos. 2,845,451 and 2,886,591). In addition, U.S. Pat. No. 3,627,820 discloses a process for polymerizing acrylic acid and acrylate monomers in the presence of a catalyst consisting of a complex compound of 2,4-pentanedione with trivalent manganese and a mercaptan.

On the other hand, polymerization inhibitors for acrylic acid, acrylates and their derivatives are well known but these inhibitors that are used commercially generally have very low vapor pressures. Although such polymerization inhibitors provide satisfactory results for the storage of acrylic acid, acrylates and their derivatives under normal conditions, they suffer from certain disadvantages. For example, when the monomers are vaporized and condensed on a cooling surface, especially those surfaces that will catalyze the polymerization of acrylates, acrylic acid and their derivatives, these monomers will polymerize and form undesirable deposits on equipment, storage vessels and the like.

These and other disadvantages in the prior art are overcome by the present invention, which provides a polymerization inhibitor for monomers of acrylic acid, acrylates and derivatives thereof, which has a vapor pressure similar to that of these monomers and, thus, will prevent polymerization on surfaces where the monomers may condense. Such a polymerization inhibitor is particularly desirable when acrylic acid, acrylates and derivatives thereof are vaporized, as for example, during the course of a distillation, and thereafter condensed to separate these monomers from other components in a mixture.

SUMMARY OF THE INVENTION

The advantages of the present invention are achieved by a composition which comprises a monomer selected from the group consisting of acrylates, methacrylates, acrylic acid, methacrylic acid and mixtures thereof, and a polymerization inhibiting amount of 2,4-pentanedione. In one embodiment of this invention, an improved process is disclosed wherein a mixture comprising a monomer selected from the group consisting of acrylates, methacrylates, acrylic acid, methacrylic acid and mixtures thereof is vaporized, and a portion of the mixture is condensed, the improvement which comprises adding a polymerization inhibiting amount of 2,4-pentanedione to the mixture before it is vaporized.

The composition and process of the present invention are particularly applicable for the prevention of polymerization of acrylic acid, acrylates and derivatives thereof, when such monomers are present in admixture with other materials, as for example, when these monomers are present as impurities in maleic anhydride produced by the partial oxidation of hydrocarbons, and especially aliphatic hydrocarbons. In such a process, hydrocarbons are oxidized to maleic anhydride by passing the hydrocarbons admixed with air or an oxygen-containing gas over a suitable catalyst at elevated temperature by techniques known to those skilled in the art. There is then provided a crude maleic anhydride fraction containing acrylates, methacrylates, acrylic acid, methacrylic acid and mixtures thereof along with other impurities and by-products in the maleic anhydride. The maleic anhydride and the above-identified monomers, impurities and by-products are then recovered by techniques known to those skilled in the art, such as for example, by condensation or solvent scrubbing. According to the process of the present invention, a polymerization inhibiting amount of 2,4-pentanedione is then added to the crude maleic anhydride, and thereafter, the maleic anhydride mixture is distilled to recover a fraction of the maleic anhydride from the mixture. In a fractional distillation column, the acrylic acid, acrylates and derivatives thereof will condense along the 2,4-pentanedione at a different point than the maleic anhydride in the distillation column because of the differences in vapor pressures. Under normal conditions, the monomers would polymerize but this is prevented by the presence of the polymerization inhibiting amount of 2,4-pentanedione.

For the purposes of this invention, the term "monomer" shall mean acrylates, methacrylates, acrylic acid, methacrylic acid and mixtures thereof. It is contemplated that these are not necessarily pure substances but may be technical grade monomers or even monomers produced in by-product reactions containing a high level of impurities, or even a small amount of the polymer.

The amount of 2,4-pentanedione, which is sometimes known commonly as acetyl acetone, can vary within wide limits depending upon the monomer, the temperature and pressure, and the presence or absence of other materials that might catalyze the polymerization. As an example, at temperatures of about 20° C. in a glass lined vessel, as little as 0.1 weight percent 2,4-pentanedione, based upon the weight of the monomer present, is effective. It has been found that 1 weight percent 2,4-pentanedione, based on the weight of the monomer, will prevent polymerization of the monomer at higher temperatures, say 60° C. to 75° C., and at higher temperatures, say 110° C., and in the presence of iron as much as 2 weight percent 2,4-pentanedione, based on the amount of monomer present, is required. Although there is no upper limit to the amount of 2,4-pentanedione that is required to prevent polymerization of the monomer, it has been found that more than about 5 weight percent, based on the weight of the monomer, is unnecessary in most instances. When the monomer is acrylic acid, at a temperature of about 110° C., it is preferred to use between about 2 and about 5 weight percent 2,4-pentanedione, based on the weight of the acrylic acid.

The polymerization of any number of monomers can be inhibited using the 2,4-pentanedione according to the present invention. Monomers that can be inhibited include acrylate monomers, such as methylacrylate, ethylacrylate, butylacrylate and the like; and methacrylate monomers, such as methylmethacrylate, ethylmethacrylate, butylmethacrylate and the like.

To polymerize the monomer containing the 2,4-pentanedione, it is only necessary to remove the 2,4-pentanedione from the monomer, and subject the monomer to conditions necessary for polymerization. The 2,4-pentanedione can be removed from the monomer by techniques known to those skilled in the art, for example, fractional crystallization, vacuum distillation and the like. On the other hand, the prior art discloses that 2,4-pentanedione complexes with trivalent manganese and a mercaptan to provide a polymerization catalyst.

DESCRIPTION OF THE PREFERRED EMBODIMENT

In one embodiment of this invention, 2,4-pentanedione is used as a polymerization inhibitor for acrylates and acrylic acid during the distillation of crude maleic anhydride.

The reaction to convert hydrocarbons to maleic anhydride is well known to those skilled in the art and requires only passing the hydrocarbon admixed with a free oxygen-containing gas, such as air or oxygen-enriched air, through a catalyst at elevated temperature. Both fluidized bed reactors and fixed-tube, heat-exchanger type reactors are satisfactory, and the details of the operation of such reactors are well known to those skilled in the art. The hydrocarbons are passed through the catalyst at a concentration of about 1.5 to about 10 volume percent hydrocarbon at a space velocity of about 100 to 4,000 cc/cc/hour to provide maleic anhydride.

The maleic anhydride that is produced can be recovered by any number of means well known to those skilled in the art. For example, the maleic anhydride can be recovered by direct condensation or by absorption in a suitable media with subsequent separation and purification of the anhydride.

In one embodiment of this invention, a dialkyl phthalate, preferably dibutyl phthalate, is used to absorb maleic anhydride from a hot mixture of gases using solvent scrubbing techniques known to those skilled in the art. A gaseous mixture from the reactor is contacted with the dialkyl phthalate while maintaining the dialkyl phthalate in the liquid phase and above the dew point of water, normally about 55° C. The solvent containing the maleic anhydride is then passed into a stripper or distillation column (or series of columns) at low pressure and elevated temperatures, say 200° C. or higher, and the maleic anhydride is then stripped from the solvent. By the process of the present invention, 2,4-pentanedione is added to the solvent before it is stripped of the maleic anhydride to insure that acrylic acid and acrylates, which are present as impurities in the maleic anhydride, do not polymerize on the cooler portions of the stripper/distillation columns. Because of the differences in vapor pressures, the acrylic acid and 2,4-pentanedione are easily separated from the maleic anhydride, which condenses at a lower temperature.

The invention is further illustrated by, but not limited to, the following Examples.

EXAMPLE I

Into each of two stoppered glass bottles was placed 5 grams of acrylic acid. Then 0.2 gram (3.85 weight percent) of 2,4-pentanedione was added to one bottle of acrylic acid. Both bottles were then placed in an oven at 90° C. for 45.5 hours and thereafter placed in an oven at 105° C. to 110° C. for 73 hours. After removal from the oven, the acrylic acid containing the 2,4-pentanedione was viscous, but the acrylic acid that did not contain the 2,4-pentanedione was solid, indicating that the 2,4-pentanedione inhibited the polymerization of the acrylic acid.

EXAMPLE II

Into a maleic anhydride absorber column are fed about 14,378 cubic meters of gaseous reaction mixture from a fixed-tube reactor converting $C_4$ aliphatic hydrocarbons to maleic anhydride. The gaseous reaction mixture contained about 460 kilograms maleic anhydride, at a pressure of about 915 torr and at a temperature of about 150° C. The gaseous reaction mixture was contacted with about 2,200 kilograms of dibutyl phthalate solvent at a temperature of about 42° C. to absorb the maleic anhydride. The solvent, leaving the absorber column contains about 456 kilograms of maleic anhydride, about 4 kilograms water, about 0.6 kilograms acetic acid and about 3.9 kilograms of acrylic acid. Thereafter, the solvent is introduced into one or more distillation-stripper columns at a temperature of about 200° C. at a pressure between about 5 torr and 10 torr. The maleic anhydride, water, acetic acid, acrylic acid and solvent are driven up the distillation-stripper column and the maleic anhydride is condensed at a temperature between about 66° C. and 70° C. The maleic anhydride is removed as a liquid reflux near the top of the stripper-distillation column, and the solvent stripped of the maleic anhydride leaves the bottom of the distillation-stripper column, is cooled to about 42° C., and is returned to the absorber column. After about 450 kilograms of maleic anhydride is recovered in this system, polymerization of acrylic acid is observed in the upper portions of the distillation-stripper column.

The polymerized acrylic acid is removed from the upper portions of the distillation-stripper column, and the recovery of maleic anhydride is resumed under the same conditions except that 156 grams of 2,4-pentanedione are added to the solvent after it leaves the absorber column, but before it enters the distillation-stripper column. After about 450 kilograms of maleic anhydride are recovered in the system, no polymerization products are observed in the upper portions of the stripper column.

Although the invention has been described in terms of specified embodiments which are set forth in considerable detail, it should be understood that this is by way of illustration only and that the invention is not necessarily limited thereto since alternative embodiments and operating techniques will become apparent to those skilled in the art in view of the disclosure. As an example, it has been shown that 2,4-pentanedione inhibits the polymerization of acrylates, methacrylates, acrylic acid, methacrylic acid and mixtures thereof, but those skilled in the art will recognize that other vinyl monomers, such as acrylonitrile, methacrylonitrile, acrylamides, methacrylamide, methylolacrylamide and esters thereof, or vinylidene chloride and the like, can be inhibited from unwanted polymerization by the teachings of the present invention. Accordingly, modifications are contemplated which can be made without departing from the spirit of the described invention.

What is claimed is:

1. In a process wherein a mixture comprising a monomer selected from the group consisting essentially of acrylate esters, methacrylate esters, acrylic acid, methacrylic acid and mixtures thereof is vaporized, and a portion of the mixture is condensed, the improvement which comprises adding a polymerization inhibiting amount of 2,4-pentanedione to the mixture before it is vaporized.

2. In a process of claim 1 wherein the mixture comprises maleic anhydride and the monomer.

3. In a process of claim 1 wherein the amount of 2,4-pentanedione is at least one weight percent, based on the weight of the monomer.

4. In a process of claim 1 wherein the amount of 2,4-pentanedione is at least two weight percent, based on the weight of the monomer.

* * * * *

UNITED STATES PATENT AND TRADEMARK OFFICE
CERTIFICATE OF CORRECTION

PATENT NO. : 4,113,574

DATED : September 12, 1978

INVENTOR(S) : Ignatius Schumacher, James E. White

It is certified that error appears in the above-identified patent and that said Letters Patent are hereby corrected as shown below:

Column 2, line 16, insert --with-- between "along" and "the".

Column 2, line 51, "110° C." should read: --100° C.--.

Signed and Sealed this

Twenty-second Day of May 1979

[SEAL]

Attest:

RUTH C. MASON
Attesting Officer

DONALD W. BANNER
Commissioner of Patents and Trademarks